United States Patent [19]
Brooks et al.

[11] Patent Number: 5,276,434
[45] Date of Patent: Jan. 4, 1994

[54] CARBON MONOXIDE CONCENTRATION INDICATOR AND ALARM

[76] Inventors: Elgin C. Brooks, 30749 E. River Rd., Perrysburg, Ohio 43551; Robert J. Burmeister, 718 Caswell Ave., Toledo, Ohio 43609; James G. Diller, 3819 Sulphur Springs Rd., Toledo, Ohio 43606

[21] Appl. No.: 864,882

[22] Filed: Apr. 3, 1992

[51] Int. Cl.$^5$ .............................................. G01N 27/00
[52] U.S. Cl. ........................................ 340/632; 73/31.02
[58] Field of Search ................... 73/23.2, 31.01, 31.02; 340/632

[56] References Cited

U.S. PATENT DOCUMENTS

| | | | |
|---|---|---|---|
| 3,305,852 | 2/1967 | Cates, Jr. | 340/632 |
| 4,091,674 | 5/1978 | Amey | 73/23.2 X |
| 4,297,689 | 10/1981 | Shaw et al. | 340/632 |
| 4,526,028 | 7/1985 | Hübner | 73/232 |
| 4,562,723 | 1/1986 | Hübner | 73/31.02 X |
| 4,706,493 | 11/1987 | Chang et al. | 73/23 |
| 4,752,761 | 6/1988 | Dolan et al. | 338/13 |
| 4,761,639 | 8/1988 | Pyke et al. | 73/23.2 X |
| 4,770,027 | 9/1988 | Ehara et al. | 73/23 |
| 4,792,433 | 12/1988 | Katsura et al. | 422/98 |
| 4,816,800 | 3/1989 | Onaga et al. | 338/34 |
| 4,860,223 | 8/1989 | Grilk | 340/632 X |
| 5,074,137 | 1/1991 | Harris et al. | 73/31.02 |

FOREIGN PATENT DOCUMENTS 100749 7/1985 Japan .................. 73/31.01

OTHER PUBLICATIONS

Block Diagram—LM 3914T LED Display Circuit National Semiconductor Linear Data Book 1980 pp. 9–107 to 9-B4.
CA4541 Programmable Timer Fact Card 158 Popular Electronics Figaro Gas Sensor TGS 822 Manual Jan. 1989.

*Primary Examiner*—Hezron E. Williams
*Assistant Examiner*—Joseph W. Roskos
*Attorney, Agent, or Firm*—Charles F. Schroeder

[57] ABSTRACT

A compact portable unit incorporating a noxious gas concentration alarm system and method adapted to setting off an alarm to warn of the presence of a dangerously high level concentration of carbon monoxide in an environment and when lower levels of concentration are present for time periods which are predetermined to be hazardous to an individual in the environment. A specific embodiment is disclosed in which two or more timed levels of carbon monoxide concentration are arranged to set off an alarm and/or automatic shutdown of the CO producing mechanism when the measured time of presence of each concentration level is hazardous to an individual in the environment.

21 Claims, 2 Drawing Sheets

CARBON MONOXIDE CONCENTRATION INDICATOR AND ALARM

FIELD OF THE INVENTION

This invention relates to apparatus and method for sensing the presence, the concentration and for providing a high level hazard alarm when noxious gases and particularly carbon monoxide are present in a given vicinity.

BACKGROUND AND PROBLEM

The problem in particular is that carbon monoxide (CO) is an odorless, colorless, lethal gas when present in an environment, such as from incomplete combustion in automobiles, airplanes, recreational vehicle heater systems or home furnaces. Carbon monoxide's particular danger is that its presence is nondetectable by the five senses. It has no scent or color and it prevails unknowingly in the atmosphere as a lethal hazard to individuals. Many deaths result from lack of knowledge that this gas is present. Other gasses may be noxious but usually they have odors. They do not have the capability of depriving persons of oxygen in the bloodstream to their brain as does carbon monoxide.

A low level concentration of carbon monoxide to an individual in an environment over a prolonged period can be hazardous as well as a high level concentration over a short period. The hemoglobin has an affinity to pick up carbon monoxide at an estimated rate 250 times greater than that for oxygen. Discomfort can be experienced with long term exposure to carbon monoxide at as low as 35 parts per million (ppm) of atmosphere. Symptoms of CO poisoning are headaches, nausea, dizziness, irritability, impaired reaction time and confusion. Continuous exposure to high concentrations will lead to convulsions, coma and death.

In this respect when the concentration level is at 200 ppm or above for a period of 2 to 3 hours the hemoglobin level may be in the order of 10% to 20% and a slight headache might be experienced to an individual in the environment. At 400 ppm for a period of 1 to 2 hours a severe headache can be expected and the hemoglobin level will be in the order of 20% to 30%. At 800 ppm for a 45 minute period convulsions can be expected and the hemoglobin level may be in the order of 30% to 40%. At 1600 ppm for a period of 45 minutes the hemoglobin level may be in the order of 50% to 60% and death might be expected.

SOLUTION

A measuring system is provided according to the present invention which, in addition to giving a visual indication of the concentration of carbon monoxide in the environment, provides a warning in the form of an audible signal, such as a horn, bells or a buzzer, when a carbon monoxide concentration of preselected level has been present in the environment for a hazardous period of time. For example, a warning alarm is sounded when a predetermined high level of concentration is present in a given atmosphere but at preselected lower concentration levels, timers are activated which measure the time of presence of the selected concentrations. At preselected times of the lower concentrations, the same high level alarm or different audible alarms are activated. A warning signal can thus be provided for any desired number of concentrations of the carbon monoxide in a given vicinity. In addition to an audible sound, means can be activated which will exert corrective measures such as by automatic shutdown of the carbon monoxide producing mechanism or initiation of manual correction when high carbon monoxide concentrations are present or when lower levels are present for periods which are hazardous.

If the alarm sounds, protective action for safety should be taken. If this is in the home, the windows and doors should be opened for fresh air, or the individual should leave the house entirely until the alarm stops. In an auto or a recreational van, fresh air should be sought and the exhaust system should be checked to assure there is no propane gas leak. In an aircraft, landing should be considered for an exhaust lead inspection.

More specifically, the invention incorporates a conventional sensing means such as a commercially available tin dioxide ceramic element which when heated changes in electrical resistance dependent upon the concentration of carbon monoxide or other noxious gasses in the vicinity in which it is placed. With the particular sensor utilized in the arrangement herein described, the resistance diminishes as the concentration levels increase. This characteristic is utilized in a voltage resistance circuit to provide an increasing voltage signal as concentration levels are increased. A quantitative signal is thus available to operate a visual indicator display of concentration levels present.

A novel aspect of the invention is that in addition to providing a direct indication of the concentration of noxious gas present as well as providing a warning signal when the concentration level is dangerously high, a signal or signals are provided when predetermined lower concentration levels are present in the vicinity for preselected time periods determined to be hazardous.

A timer is activated for each selected level of concentration for which a warning is to be provided. Other than the immediate alarm being sounded when a high hazardous concentration level is present, a warning alarm is activated when a preselected period is counted off by the timer for a concentration level higher than that which initiates its operation. As indicated, any number of such lower concentration levels can be so timed by different timers to provide warning signals. The unit exemplifying the invention is described herein in relation to three hazard levels, two of which are timed to operate the alarm when a predetermined time period of presence of each such hazard level is present. It will be understood, however, that any of a number of additional levels of alarm may be incorporated in the unit each measured for a different alarm time period corresponding to a concentration at the area above that which has been found to be hazardous. In this sense the timing means provides a signal to the alarm at times of length inversely related to the concentration of noxious gas sensed in the environment. In addition to actuation of an audible alarm, signals can be sent to a remotely located monitoring station or stations to call for corrective or emergency action when necessary.

In the specific arrangement described, the visual quantitative indicator is in the form of a series of light emitting diodes (LEDs), each of which is activated at a different voltage level determined by the voltage supplied from the sensor and applied to a resistance circuit associated with the series of LEDs.

The signal from the sensor is applied to a series of ten comparators, each of which is biased to a different comparison level by the resister circuit comprised of a string of resisters. For each 125 mV that the input signal increases, a comparator will switch on another indicating LED. Thus the number of LEDs energized indicate the level of concentration of noxious gas present.

Although the arrangement herein described will sense a number of noxious gasses, such as alcohol, acetone, benzene, ethanol, m-Hexane, isobutane, methane, propane and gasoline, it is most sensitive to methane and carbon monoxide, the most prevalent responsible for deaths from poisoning due to inhalation. The system exemplified provides an immediate warning signal when the concentration of carbon monoxide is 400 parts per million (ppm) and a warning after 1½ hours when the concentration is 200 ppm or after 6 hours for a concentration of 50 ppm.

An object of the invention is to provide a compact portable CO sensing unit incorporating a system which will perform the above described warning functions.

A feature of the invention is its capability to provide a signal which can be made visual as well as audible and initiate corrective measures when high concentrations of a noxious gas, particularly carbon monoxide, is present in a given atmosphere.

Another if not more important feature is the capability of the system to provide warning signals when low level concentrations of a hazardous gas, principally carbon monoxide, is present for time periods which by experience have been determined to be hazardous.

In addition to an audible alarm, the unit can be arranged to energize a relay or relays associated with any other number of functions such as to shut off of an automobile engine where the concentration is sensed in the passenger compartment, or to shut off a heating unit giving off carbon monoxide into the sensed atmosphere which reaches a level of concentration which after a period of time of exposure is hazardous to persons in the vicinity.

Still another feature of the invention is that the variables of time and concentration are tied together such that if the concentration is relatively low but is present for a prolonged period, am alarm is activated. If the concentration is high, the time function for setting off the alarm is relatively short.

A still further feature of the invention is its capability of correlating the concentration of carbon monoxide and timed alarms to human responses wherein a low concentration of carbon monoxide can be tolerated for a considerable period and a high concentration can be tolerated only for a short period of time before presence of carbon monoxide becomes hazardous to life.

Other objects and features which are believed to be characteristic of our invention are set forth with particularity in the appended claims. Our invention, however, both in organization and manner of construction, together with further objects and features thereof may be best understood by reference to the following description taken in connection with the accompanying drawing.

DRAWINGS

DETAILED DESCRIPTION

Figure 1:
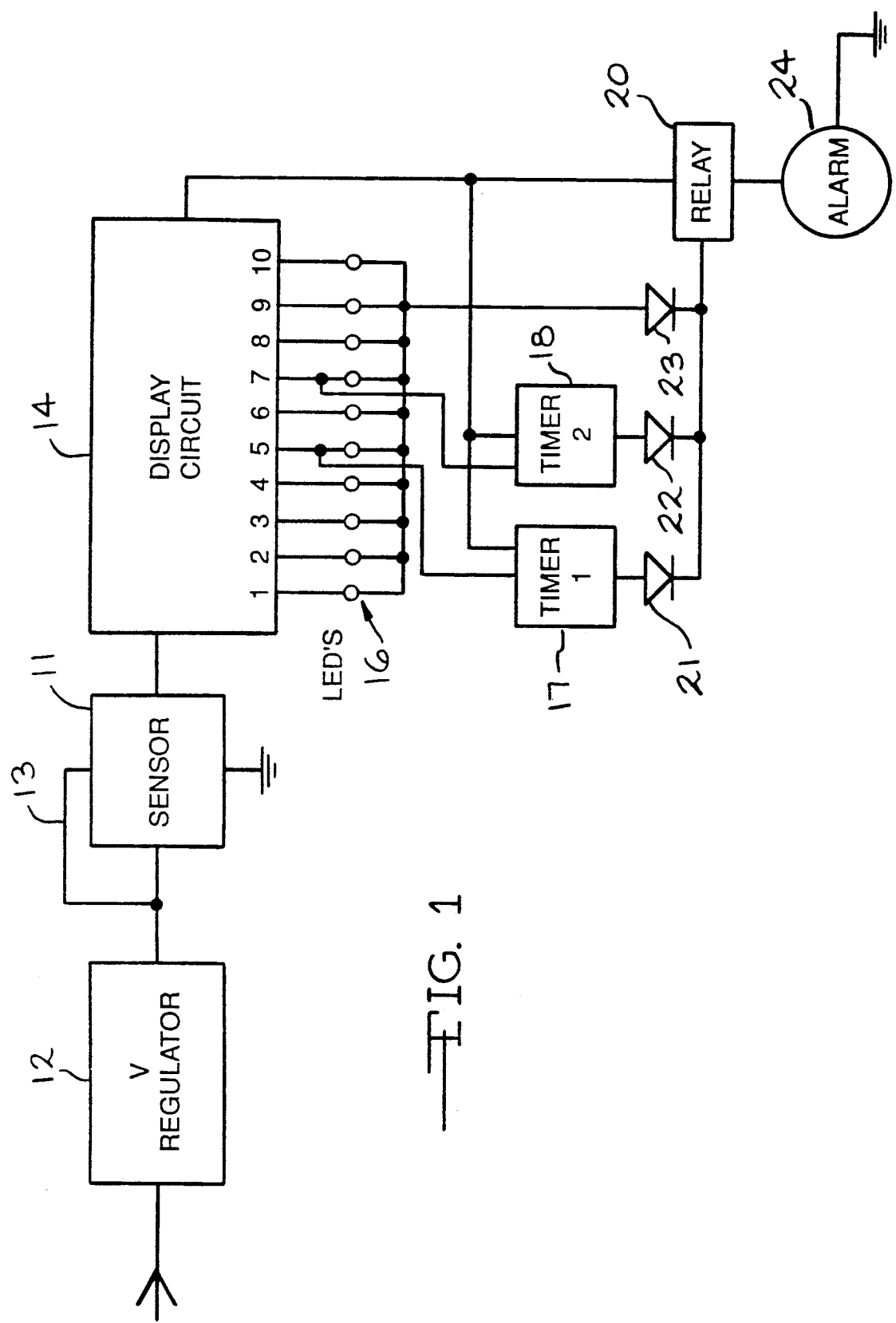
FIG. 1 is a block diagram of the electrical circuit for display concentration level and timing the presence of carbon monoxide in an environment according to the present invention.

The block diagram of FIG. 1 shows a sensor 11 supplied with a voltage from a voltage regulator 12. As indicated, the sensor is a conventional tin dioxide ceramic element which is formed on an alumina ceramic tube 30. The sensor element requires heat to operate effectively and accordingly is heated by a heater coil 29 located inside the tube 30, the heater being energized by way of a branch lead 13 extending from the voltage regulator connection. Before it is heated, the metal is usually in oxidized condition because of the oxygen present in the atmosphere but the oxygen is burned off by heating the metal. The resistance of the heated sensor changes with various concentrations of gasses in the environment. Reducing gasses and vapors make the sensor resistance decrease. The sensor is particularly highly sensitive to vapors of organic solvents. The particular sensor unit utilized in the illustrated circuit is a Figaro TGS 822 gas sensor supplied by Figaro U.S.A., Inc., Wilmet, Ill.

The signal supplied from the sensor is fed to a display circuit 14 having a series 16 of light emitting diodes (LEDS), ten in number which provide a quantified visual indication of the concentration of gas in the vicinity based upon the magnitude of the signal supplied from the sensor. The LEDs are numbered 1 to 10, each representing a different level of concentration of noxious gas sensed.

The system is calibrated particularly to warn of the presence and concentration of carbon monoxide. When the concentration of CO is such that the fifth LED in the series, representing 50 ppm concentration, is energized, a timer 17 is activated along with the LED 5 to start the count of a 6 hour period before a signal is supplied therefrom through a diode 21 to a relay 20 which when activated energizes an audible alarm 24. Thus when a concentration of approximately 50 ppm of carbon monoxide is present in the vicinity of the sensor 11 for a period of 6 hours, the audible alarm 24 is sounded.

Each of the LEDs in order represents an advance in concentration of CO in the atmosphere surrounding the sensor. The sensor signal is nonlinear relative to the concentration of CO sensed but by matching the span of the display circuit 14 to the concerned signal range of the sensor, preselected LEDs in the series 16 are energized as representative of specific CO levels.

When the level of concentration is approximately 200 ppm or higher, the seventh LED in the series illustrated in FIG. 1 is energized along with the second timer 18 to count off a shorter period of 1½ hours, whereupon it operates to provide a signal to energize the relay 20 for activation of the audible alarm 24. That is, when the concentration level is between approximately 50 ppm and 200 ppm the timer 17 counts out a period of 6 hours, but if the concentration reaches and remains at a level of 200 ppm and above the timer 18 energizes the audible alarm within 1½ hours. In the event that the concentration level falls below a critical level being timed, such as when fresh air is introduced into the environment, the respective timer involved is reset to zero for start of a new cycle of measurement should the critical concentration of CO again arise.

The LED indicator circuit in a sense itself acts as a digital counter which activates the timers at preselected indicated levels. As an alternate arrangement, each timer can be activated by separate means responsive to a specific level of concentration. In this sense the timer acts as a time delay in setting off an alarm to indicate a prevailing level of concentration of CO.

In the event that the concentration reaches a level in the order of 400 ppm or above, LED 9 in the series 16 is energized and a direct connection is made to the relay 20 to sound off the alarm 24. Thus any concentration level of carbon monoxide above approximately 400 ppm will activate the audible alarm almost immediately.

Figure 2:
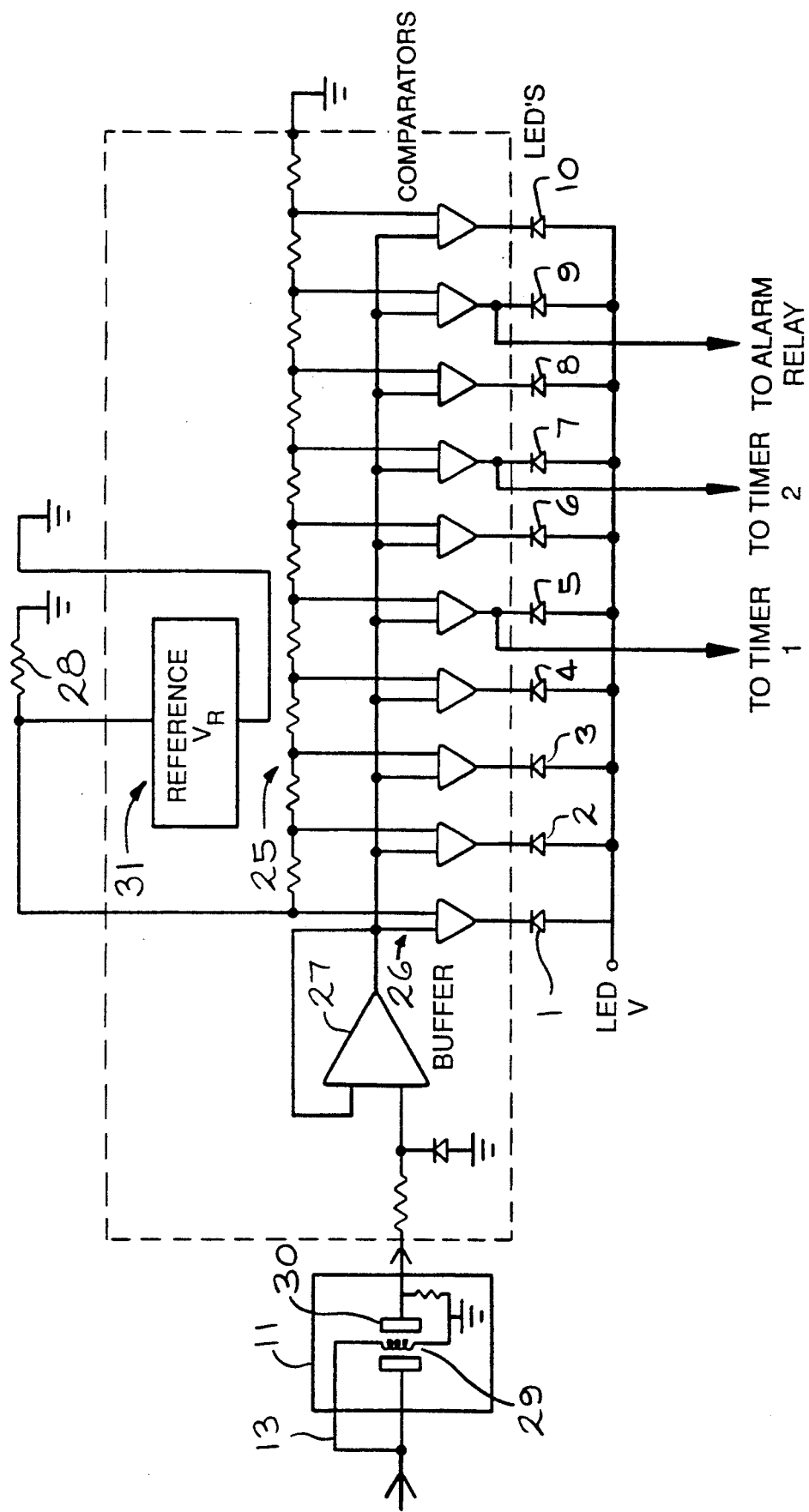
FIG. 2 is a more detailed block diagram of the electrical circuit for the sensor and display portion of the circuit illustrated in FIG. 1.

FIG. 2 illustrates the display circuit in more detail wherein a string of resistances 23 corresponding in number to the number of LEDs 1 to 10 in the circuit are each associated with one of a string of ten comparators 26. A high input impedance buffer 27 including a high current limiting resistor operates with signals from ground to for example, 12 volts and is thus protected against reverse and over-voltage signals. The signal from the sensor is applied to the series of comparators 26, each of which is biased to a different comparison level by the resistor string 25. The resistor string is connected to an internal reference voltage 31 by way of a resistor divider 28 which provides a voltage such as 1.25 volts. The reference voltage is divided for example into 10 increments and the circuit is arranged so that when the sensor signal increases to the level matched to one of the increments, a corresponding comparator 26 will energize its associated indicating LED 16.

A display circuit found suitable is an LM3914 integrated circuit which senses analog voltage under certain conditions and where magnitudes of concentration of much higher level are desired to be alarmed, a LM3915 integrated circuit may be used which senses analog voltage but drives the 10 LEDs providing a logarithmic 3dB/step display. Where deemed desirable, two or more display circuit units each having 10 display LED's can be connected in series to divide the spectrum of concentration levels represented between 20, 30 or more multiples of 10 LED indicators of concentration level. Thus each LED can be arranged to represent a smaller more exact indication of an advance, such as a 25 ppm step or less.

The timers found to be reliably suitable for the present invention are industry standard CD 4541 timers available from Harris Semiconductor Co. and National Semiconductor Company. Although a specific display circuit and specific timers are referred to as representative for use in the invention, it will be recognized that a number of different types of timers might be incorporated in the overall circuitry without deviating from the concept of the present invention.

The unit of the invention may be energized by way of an automotive plug in a cigarette lighter or with a voltage reducing inverter unit plugged into a 110 volt AC circuit. Normal power consumption for the overall circuit is 0.3 amps increasing to about 0.4 amps when all LEDs and the alarm are active. The alarm output may be optically isolated from the sensor circuit allowing considerable variation in connections to alternate alarm systems as may be desired.

In view of the foregoing it will be understood that many variations of the arrangement of our invention can be provided within the broad scope of the principles embodied therein. Thus, while a particular preferred embodiment of our invention has been shown and described herein, it is intended by the appended claims to cover all such modifications which fall within the true spirit and scope of the invention.

We claim:

1. A hazardous noxious gas alarm system comprising
   a noxious gas sensor which provides a continuous electrical signal corresponding to the concentration of noxious gas in the environment,
   a meter responsive to the signal from said sensor which continuously indicates the level of concentration of noxious gas in said environment,
   at least one timer activated subject to an indication of said meter of a preselected level of concentration of noxious gas signaled by said sensor known to be hazardous after a predetermined time period, said timer being arranged to measure the time of presence of said preselected level of concentration of noxious gas,
   an alarm associated with said timer arranged to be activated upon measurement of said predetermined hazardous period of time of presence of said level of concentration.

2. A hazardous gas alarm system as set forth in claim 1 in which at least two timers are provided each of which is operationally activated above a different preselected hazardous level of concentration signaled by said sensor and each measuring a different predetermined period of time for activation of said alarm.

3. A hazardous gas alarm system as set forth in claim 2 in which each timer operates a different alarm.

4. A hazardous gas alarm system as set forth in claim 1 in which a signal is sent to a remotely located monitoring station responsive to measurement of a predetermined period of time by said timer.

5. A hazardous gas alarm system as set forth in claim 1 in which the timer is set to activate said alarm specifically when a preselected hazardous concentration of carbon monoxide occurs.

6. A hazardous gas alarm unit according to the system of claim 1 in which said meter responsive to the signal from said sensor is a digital indicating meter.

7. A hazardous gas alarm unit as set forth in claim 6 in which the digital indication of said meter is provided by a series of light emitting diodes.

8. A hazardous gas alarm unit as set forth in claim 7 in which said timer is activated when a light emitting diode corresponding to a preselected hazardous level of concentration of noxious gas is energized.

9. A method of providing a warning when noxious gasses are present in an atmosphere for a time period predetermined to be hazardous comprising sensing the concentration of noxious gas in the environment,
   providing a continuous electrical signal corresponding in level to the concentration level of noxious gas in the environment,
   timing the presence of gas above a preselected concentration level, and
   activating an alarm upon measurement of a predetermined period of presence of said preselected concentration of noxious gas in the environment.

10. A method of providing warning of the presence of noxious gas as set forth in claim 9 in which an indication of the presence of noxious gas is visually indicated.

11. A method as set forth in claim 10 in which the indication of presence of noxious gas is visually quantified.

12. A method of warning of the presence of hazardous gas as set forth in claim 10 in which a plurality of warning indications is given,
   each indication being responsive to a different preselected level of concentration of noxious gas for a respective period determined to be hazardous.

13. A carbon monoxide hazard warning system comprising
 a carbon monoxide sensor which provides a continuous signal representative of the concentration of carbon monoxide in an environment,
 at least one timer responsive to a preselected concentration signal from said sensor to initiate measurement of a predetermined time of continuous presence of the preselected concentration of carbon monoxide in the environment,
 said tinter being arranged to provide a signal upon measurement of said predetermined time,
 an alarm responsive to said timer signal to warn of the prevalence of carbon monoxide gas for a hazardous period.

14. A warning system as set forth in claim 13 in which means is provided for activating said alarm directly when the concentration level of carbon monoxide is dangerously higher than said preselected concentration.

15. A carbon monoxide hazard warning system as set forth in claim 13 including a meter responsive to the signal at said sensor which visually indicates the concentration of carbon monoxide in the environment.

16. A carbon monoxide hazard warning system as set forth in claim 13 in which said alarm is an audible alarm.

17. A carbon monoxide hazard warning system as set forth in claim 13 in which said alarm includes means effective to automatically shut down a mechanism from which carbon monoxide is supplied to the environment.

18. A method of providing a warning when the presence of carbon monoxide in a given environment is prevalent for a hazardous period comprising
 sensing the presence of carbon monoxide in the environment,
 providing a signal representative of the concentration of carbon monoxide sensed in the environment,
 timing the continuous presence of carbon monoxide sensed responsive to a continuous signal representing a concentration greater than a preselected concentration,
 providing a time signal upon measurement of a predetermined hazardous time of presence of carbon monoxide sensed above said preselected concentration, and
 providing a warning alarm responsive to said time signal to indicate the existence of a prevailing hazardous condition.

19. The method of providing a warning according to claim 18 wherein a visual indication representative of the concentration level of carbon monoxide is provided in response to the signal of carbon monoxide sensed.

20. The method of claim 18 in which at least two timed alarm signals are provided each being responsive to the continuous presence of a different preselected hazardous concentration of carbon monoxide.

21. A noxious gas hazard warning system comprising
 a noxious gas sensor which provides an electrical signal representative of the concentration of noxious gas in the environment,
 timer means responsive to said electrical signal from said sensor adapted to provide an alarm activating signal,
 alarm means responsive to said alarm activating signal,
 said timer means being arranged to provide said activating signal to said alarm means at times of length inversely related to the continuous presence of noxious gas above preselected magnitudes of concentration of noxious gas sensed in the environment.

* * * * *